(12) United States Patent
Royo et al.

(10) Patent No.: US 7,211,538 B2
(45) Date of Patent: May 1, 2007

(54) CATALYTIC SYSTEMS FOR THE POLIMERIZATION AND COPOLIMERIZATION OF ALPHA-OLEFINS

(75) Inventors: Jose Sancho Royo, Madrid (ES); Gerardo Hidalgo Llinás, Madrid (ES); Antonio Muñoz-Escalona Lafuente, Madrid (ES); Francisca Martínez Núñez, Madrid (ES); Carlos Martín Marcos, Madrid (ES); Pilar Lafuente Cañas, Madrid (ES); Begoña Peña García, Madrid (ES)

(73) Assignee: Repsol Quimica S.A., Madrid (ES)

( * ) Notice: Subject to any disclaimer, the term of this patent is extended or adjusted under 35 U.S.C. 154(b) by 0 days.

(21) Appl. No.: 10/893,754

(22) Filed: Jul. 16, 2004

(65) Prior Publication Data

US 2005/0065019 A1   Mar. 24, 2005

Related U.S. Application Data

(62) Division of application No. 08/961,956, filed on Oct. 31, 1997, now abandoned.

(30) Foreign Application Priority Data

Oct. 31, 1996   (ES)   ................................. P9602310

(51) Int. Cl.
*B01J 31/00* (2006.01)
*C08F 4/44* (2006.01)

(52) U.S. Cl. ...................... 502/155; 502/102; 502/103; 502/117; 502/127; 502/152; 502/160

(58) Field of Classification Search .............. 502/103, 502/155, 102, 117, 150, 152, 127, 160; 526/160, 526/127
See application file for complete search history.

(56) References Cited

U.S. PATENT DOCUMENTS

| | | | |
|---|---|---|---|
| 3,184,416 A | 5/1965 | Mottus | ........................ 252/429 |
| 3,440,237 A | 4/1969 | Mottus | ........................ 260/94.9 |
| 4,005,046 A | 1/1977 | Chandra et al. | ............. 252/428 |
| 4,394,294 A | 7/1983 | Gryaznov et al. | ........... 252/430 |
| 4,542,199 A | 9/1985 | Kaminsky et al. | ............ 526/160 |
| 4,939,217 A | 7/1990 | Stricklen | ..................... 526/114 |
| 5,057,475 A * | 10/1991 | Canich et al. | ............... 502/104 |
| 5,064,797 A | 11/1991 | Stricklen | ..................... 502/111 |
| 5,071,808 A * | 12/1991 | Antberg et al. | .............. 502/107 |
| 5,202,398 A | 4/1993 | Antberg et al. | .............. 526/129 |
| 5,332,706 A | 7/1994 | Nowlin et al. | ............... 502/107 |

(Continued)

FOREIGN PATENT DOCUMENTS

DE   1 022 382   1/1958

(Continued)

OTHER PUBLICATIONS

U.S. Appl. No. 08/961,346, filed Oct. 30, 1997, Royo et al.

Blümel, J., "Reactions of Ethoxysilanes with Silica: A Solid-State NMR Study," *J. Am. Chem. Soc.* vol. 117, No. 7, pp. 2112-2113 (1995).

Chien, J.C.W., et al., "Olefin Copolymerization with Metallocene Catalysts. III. Supported Metallocene/Methylaluminoxane Catalyst for Olefin Copolymerization," *Journal of Polymer Science, Part A: Polymer Chemistry*, vol. 29, pp. 1603-1607 (1991).

(Continued)

*Primary Examiner*—Karl Group
(74) *Attorney, Agent, or Firm*—Ladas & Parry LLP

(57) ABSTRACT

Catalyst component for the polymerization of alpha-olefins in solution, in suspension, in gas phase at low and high pressure and temperature or in mass at high pressures and high or low temperatures, characterized in that is defined by general formulas I or II

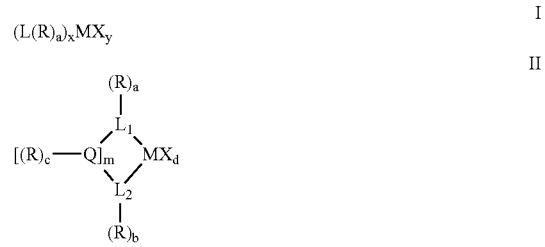

wherein:
R, equal to or different from each other, is hydrogen or a radical which contains from 1 to 20 carbon atoms; this group optionally contains heteroatoms of groups 14 to 16 of the periodic table of the elements and boron; at least one group R contains a group $OSiR'''_3$,
Q is selected from a group comprising: boron or an element from groups 14 or 16 of the periodic table; m value can change from 1 to 4 and it preferably is 1 or 2;
L, equal to or different from each other, is a cyclic organic group united to M through a π bond, or it is an atom from groups 15 or 16 of the periodic table;
$L_1$ and $L_2$, equal to or different from each other, have the same meaning of L;
M is a metal from groups 3, 4, 10 of the periodic table, lanthanide or actinide.
X, equal to or different from each other, is selected from a group comprising: halogen, hydrogen, OR''', $N(R''')_2$, $C_1$–$C_{20}$ alkyl or $C_6$–$C_{20}$ aryl; wherein R''' is selected from the group comprising: $C_1$–$C_{20}$ alkyl, $C_3$–$C_{20}$ cycloalkyl, $C_6$–$C_{20}$ aryl, $C_7$–$C_{20}$ alkenyl, $C_7$–$C_{20}$ arylalkyl, $C_7$–$C_{20}$ arylalkenyl or alkylaryl, linear or branched;
x is 1 or 2, y is 2 or 3 in such a way that x+y=4.
d ranges from 0 to 2;
a, b and c are integers from 0 to 10, in such a way that a+b+c≧1.

18 Claims, 2 Drawing Sheets

U.S. PATENT DOCUMENTS

| | | | |
|---|---|---|---|
| 5,391,789 A | 2/1995 | Rohrmann | 556/11 |
| 5,416,228 A | 5/1995 | Ewen et al. | 556/7 |
| 5,466,766 A * | 11/1995 | Patsidis et al. | 526/129 |
| 5,504,232 A | 4/1996 | Winter et al. | 556/7 |
| 5,602,067 A | 2/1997 | Nowlin et al. | 502/104 |
| 5,627,246 A * | 5/1997 | Langhauser et al. | 526/128 |
| 5,731,253 A | 3/1998 | Sangokoya | 502/102 |
| 5,747,404 A | 5/1998 | Nagy et al. | 502/104 |
| 5,753,769 A | 5/1998 | Ueda et al. | 525/323 |
| 5,780,659 A | 7/1998 | Schmid et al. | 556/11 |
| 5,824,620 A * | 10/1998 | Vega et al. | 502/117 |
| 5,846,895 A | 12/1998 | Gila et al. | 502/107 |
| 5,861,352 A | 1/1999 | Gila et al. | 502/155 |
| 5,892,079 A | 4/1999 | Wilson, Jr. | 556/11 |
| 5,910,463 A | 6/1999 | Ernst et al. | 502/107 |
| 5,914,044 A | 6/1999 | Lindoy et al. | 210/670 |
| 5,955,625 A | 9/1999 | Canich | 556/7 |
| 5,977,392 A * | 11/1999 | Royo et al. | 556/11 |
| 5,986,025 A * | 11/1999 | Huh et al. | 526/119 |
| 6,018,064 A * | 1/2000 | Mendez Llatas et al. | 556/11 |
| 6,087,293 A | 7/2000 | Carnahan et al. | 502/158 |
| 6,114,555 A | 9/2000 | Llinás et al. | 556/11 |
| 6,133,187 A * | 10/2000 | Vega et al. | 502/103 |
| 6,143,685 A * | 11/2000 | Llinas et al. | 502/152 |
| 6,268,518 B1 | 7/2001 | Resconi et al. | 556/43 |
| 6,635,778 B1 * | 10/2003 | Royo et al. | 556/11 |
| 6,825,369 B1 * | 11/2004 | Stevens et al. | 556/7 |
| 2003/0144135 A1 | 7/2003 | Llinas et al. | 502/103 |
| 2003/0191013 A1 | 10/2003 | Lafuente et al. | 502/117 |
| 2003/0195109 A1 | 10/2003 | Royo et al. | 502/117 |
| 2005/0065018 A1 | 3/2005 | Llinás et al. | 502/152 |

FOREIGN PATENT DOCUMENTS

| | | |
|---|---|---|
| DE | 26 08 863 | 9/1977 |
| DE | 37 18 888 | 12/1988 |
| DE | 38 40 772 | 6/1990 |
| EP | 0 206 794 A1 | 12/1986 |
| EP | 0 260 130 A1 | 3/1988 |
| EP | 0 277 004 A1 | 8/1988 |
| EP | 0 293 815 A1 | 12/1988 |
| EP | 0 295 312 A1 | 12/1988 |
| EP | 0 314 797 A1 | 5/1989 |
| EP | 0 323 716 A1 | 7/1989 |
| EP | 0 336 593 A1 | 10/1989 |
| EP | 0 361 866 A1 | 4/1990 |
| EP | 0 367 503 A1 | 5/1990 |
| EP | 0 368 644 A1 | 5/1990 |
| EP | 0 372 414 A2 | 6/1990 |
| EP | 0 416 815 B1 | 3/1991 |
| EP | 0 420 436 B1 | 4/1991 |
| EP | 0 426 637 A2 | 5/1991 |
| EP | 0 474 391 A2 | 3/1992 |
| EP | 0 628 566 A1 | 12/1994 |
| EP | 0 633 272 B1 | 1/1995 |
| EP | 0 668 295 B1 | 8/1995 |
| EP | 0 757 053 A2 | 2/1997 |
| EP | 0 757 992 A1 | 2/1997 |
| EP | 0 416 815 A2 | 8/1997 |
| EP | 0 799 838 A1 | 10/1997 |
| EP | 0 802 203 A1 | 10/1997 |
| EP | 0 839 833 A2 | 5/1998 |
| EP | 0 839 836 A1 | 5/1998 |
| GB | 2 092 017 | 8/1982 |
| JP | 1 085 141 A | 3/1989 |
| SU | 828471 A | 11/1983 |
| WO | 92/05203 | 4/1992 |
| WO | 94/03506 | 2/1994 |
| WO | 94/07928 | 4/1994 |
| WO | 97/19959 | 6/1997 |

OTHER PUBLICATIONS

Chien, J.C.W., et al., "Olefin Copolymerization with Metallocene Catalysts. III. Supported Metallocene/Methylaluminoxane Catalyst for Olefin Copolymerization," *Journal of Polymer Science, Part A: Polymer Chemistry*, vol. 29, pp. 1609-1613 (1991).

Chien, J.C.W., et al., "Zirconocenium Cation Catalysis of Propene Polymerization," *Makromol. Chem., Macromol. Symp.*, vol. 66, pp. 141-156 (1993).

Cihlar, J., et al., "Influence of Water in Ethylene Polymerization Catalyzed by Titanocene Systems," *Makromol. Chem.*, vol. 179, pp. 2553-2558 (1978).

Ciruelos, S., et al., "New Silyl-Substituted Cyclopentadienyl Titanium and Zirconium Complexes. X-ray Molecular Structures of $[TiCl_2\{\mu\text{-}(OSiMe_2\text{-}\eta^5\text{-}C_5H_4)\}]_2$ and $[ZrCl_2\{\mu\text{-}[(\eta^5\text{-}C_5H_4)SiMe_2OSiMe_2\,(\eta^5\text{-}C_5H_4)]\}]$," *Organometallics*, vol. 14, pp. 177-185 (1995).

Collins, S., et al., "Polymerization of Propylene Using Supported, Chiral, *ansa*-Metallocene Catalysts: Production of Polypropylene with Narrow Molecular Weight Distributions," *Macromolecules*, vol. 25, pp. 1780-1785 (1992).

Cotton, F.A., et al., *Advanced Inorganic Chemistry, A Comprehensive Text*, 4th Edition, John Wiley & Sons, p. 395 (1980).

Dias, H.V., et al., "Preparation of Group 4 metal complexes of a bulky amido-fluorenyl ligand," *Journal of Organometallic Chemistry*, vol. 508, pp. 91-99 (1996).

Dubois, L.H., et al., "Dehydroxylated Silica Surfaces," *J. Am. Chem. Soc.*, vol. 115, pp. 1190-1191 (1993).

"Group Notation Revised in Periodic Table," *Chemical & Engineering News*, vol. 63, No. 5, pp. 26-27 (Feb. 4, 1985).

Kesti, et al., "Homogenous Ziegler-Natta Polymerization of Functionalized Monomers Catalyzed by Cationic Group IV Metallocenes," *J. Am. Chem. Soc.*, vol. 114, pp. 9679-9680 (1992).

Nugent, et al., "Zirconium-Mediated Ring Construction from Dienes: Remarkable Effect of Ligands on Stereochemistry," *J. Am. Chem. Soc.*, vol. 111, pp. 6435-6437 (1989).

Plenio, et al., "$\eta^5$-Complexes of cyclopentadienylsilylethers ($C_5H_4OSiR_3$) and hydroxycyclopentadiene ($C_5H_4OH$) with titanium and zirconium chlorides," *Journal of Organometallic Chemistry*, vol. 544, pp. 133-137 (1997).

Reichert, K.H., et al., "Zur Kinetik der Niderdruckpolymerization . . . ," *Die Makromolekulare Chemie*, vol. 169, pp. 163-176 (1973).

Sinn, H., et al., "Ziegler-Natta Catalysis," *Advances in Organometallic Chemistry*, vol. 18, pp. 99-149. (1980).

Wilkinson, et al., "Bis-cyclopentadienyl derivatives of some transition elements," *J. Am. Chem. Soc.*, vol. 75, pp. 1011-1012 (1953).

Yasuda, et al., "Rare earth metal initiated polymerizations of polar and nonpolar monomers to give high molecular weight polymers with extremely narrow molecular weight distribution," *Macromol. Chem. Phys.*, vol. 196, pp. 2417-2441 (1995).

\* cited by examiner

Figure I
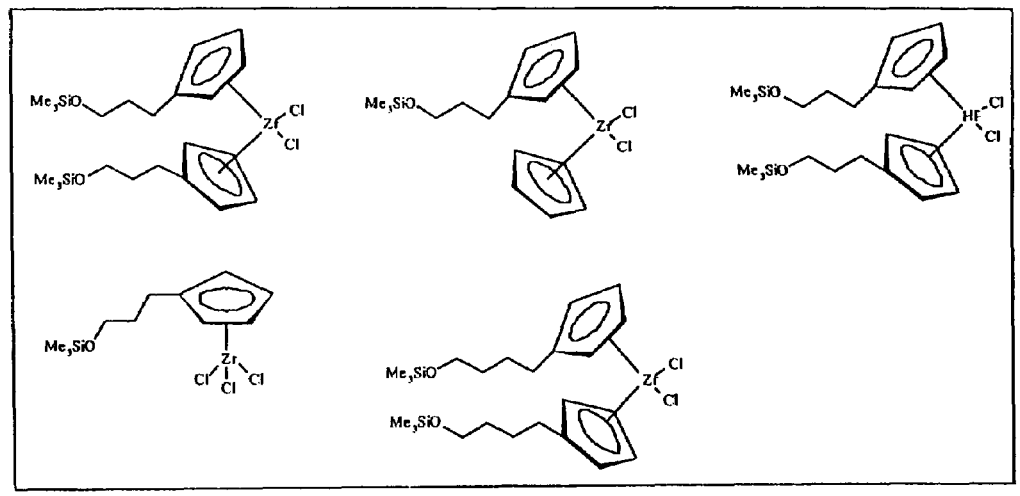
Figure II
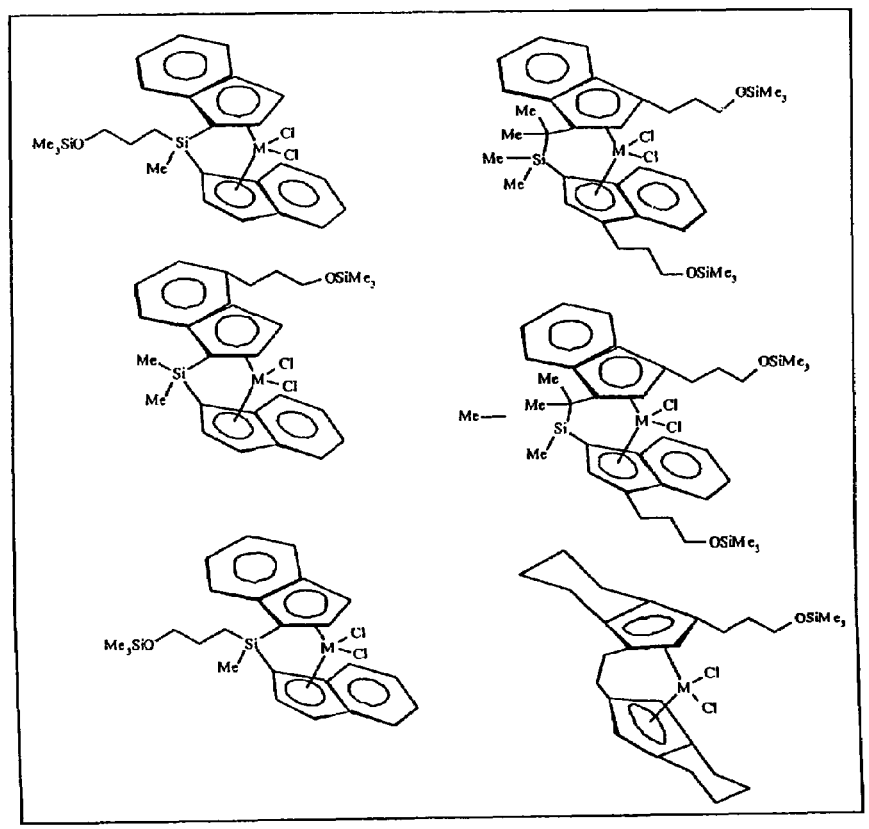

Figure III
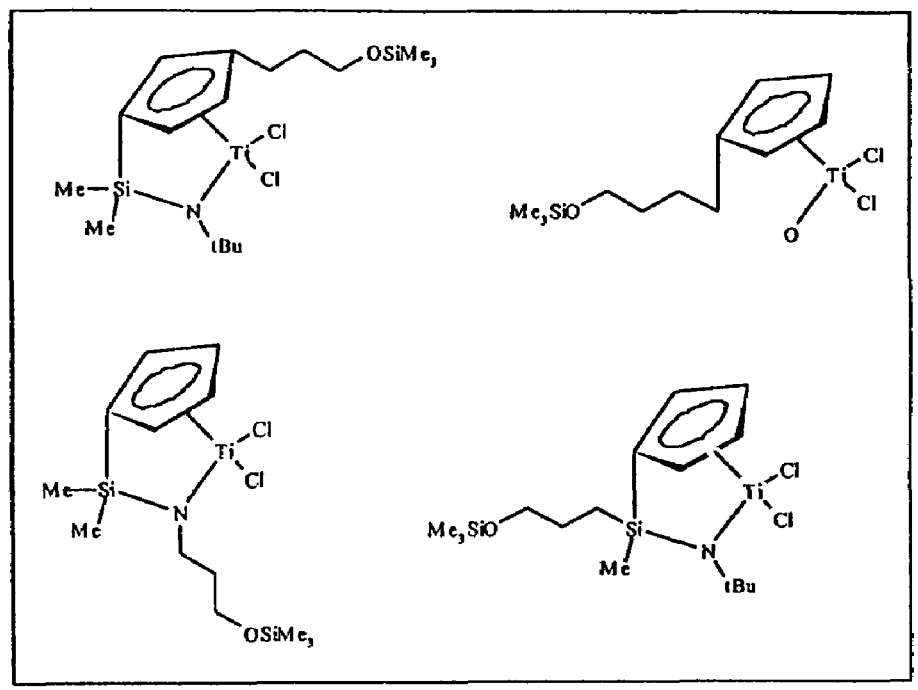
Figure IV
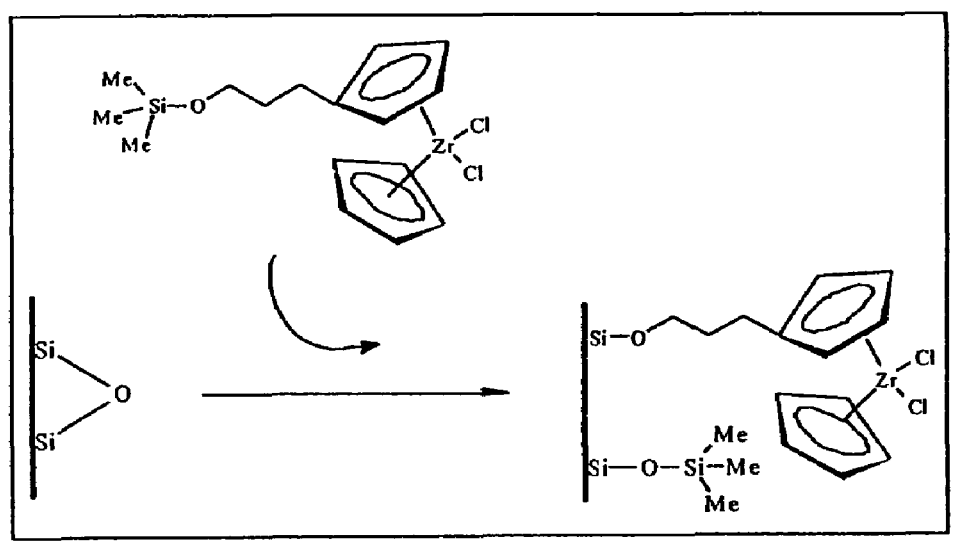

CATALYTIC SYSTEMS FOR THE POLIMERIZATION AND COPOLIMERIZATION OF ALPHA-OLEFINS

This patent application is a divisional application of U.S. patent application Ser. No. 08/961,956, filed on Oct. 31, 1997 now abandoned. Incorporated herein by this reference is Spanish Appln. No. P9602310, filed on Oct. 31, 1996. U.S. application Ser. No. 08/961,956 claims priority under 35 U.S.C. 119 to Spanish Appln. No. P9602310, filed on Oct. 31, 1996.

The present invention relates to new inetallocene catalysts which can be easily heterogenized on an inorganic support.

STATE OF THE ART

Organocomplexes of elements belonging to group IV, in combination with alkylaluminoxanes and/or boron compounds, lead to the formation of polymerization catalysts, whose activities are sometimes better than those obtained with the typical Ziegler-Natta catalysts (Makrom. Chem. 179, 2553 (1978) and 169, 163 (1973), DE 1022382, U.S. Pat. No. 3,184,416, U.S. Pat. No. 3,440,237, EP 277004 and EP 426637).

It is very well known that homogeneous catalytic systems present a disadvantage: when they are used in suspension polymerization processes, a part of the produced polymer adheres to the reactor walls; this effect is technically called "reactor fouling". Besides, in most cases, the particle size of the obtained polymer is very small and the apparent density is low, thus the industrial production is reduced. In order to prevent the reactor from fouling and to control the size and the morphology of the polymer particles which are formed, the homogeneous system can be supported on an inorganic oxide.

In the last years three different preparatory strategies have been used in order to reach this aim: cocatalyst heterogenization, metallocene heterogenization or heterogenization of both components on a fit support.

Several patents describe heterogeneous catalyst synthesis through processes initially based on the cocatalysts fixation onto the support.

U.S. Pat. No. 4,939,217 and U.S. Pat. No. 5,064,797 patents describe a heterogenization process based on the preparation "in situ" of aluminoxane on the support. The method consists in bubbling an inert humidified gas directly inside a solution of an aluminium alkyl in the presence of the support. When an organocomplex solution is added to this heterogenized cocatalyst, the catalyst is heterogenized.

Patents EP 323716, EP 361866, EP 336593, EP 367503, EP 368644 and U.S. Pat. No. 5,057,475 describe a different process from the previous one. In this case the cocatalyst is heterogenized through direct reaction of the aluminium alkyl with the superficial hydratation water molecules of the support. In a similar way to the one described in the previous patents, the organocomplex fixation is then obtained through close contact of an organocomplex solution with a suspension of the modified support.

In both cases it may happen that part of the aluminium cocatalyst is not homogeneously distributed on the support surface. Besides, it is rather difficult that, going from one preparation to another, you succeed in exactly reproducing the heterogenized aluminoxane structure and molecular weight. Another serious disadvantage is the migration of the active species into the homogeneous phase during the polymerization reaction.

EP 293815 describes the metallocene fixation according to the reactivity of the alcoxysilane functional group ($Me_2(EtO)Si-$) with superficial hydroxy groups of the inorganic oxide. The activity in polymerization is not very high, probably because a high percentage of the organocomplex is deactivated. An additional disadvantage are the low yields obtained in the preparation of this type of functionalized organometallic compounds.

The object of the present invention is to avoid these disadvantages through a process for synthesizing supported catalysts for (co)polymerization of ethylene and alpha-olefins with 3 or more carbon atoms, such as propene, 1-butene, 1-pentene, 1-hexene 4-methyl-1-pentene and 1-octene. Differently from other more conventional methods, this heterogenization process is based on the reactivity of $OSiR''_3$ functional groups of the organo-complexes with the superficial reactive groups of the catalytic support. Predictably, the fixation of this type of metallocenes, functionalized with groups $OSiR''_3$, is due, as it is described in FIG. IV, to the reaction between the groups—$OSiR''_3$ of the organometallic complexes and the reactive groups of the support.

Another object of the present invention is the use of the organometallic complexes of formula I and II as homogeneous catalysts for olefins homopolymerization and copolymerization.

Thanks to the methods described in the present invention, heterogeneous catalysts call be obtained; they allow to effectively control the morphology and the distribution of particle sizes, with a regular growth of the polymer around the catalyst particles.

DETAILED DESCRIPTION OF THE INVENTION

The present invention relates to homogeneous and heterogeneous catalytic systems containing metallocene complexes of transition metals with al least one group $R-OSiR''_3$ potentially reactive to support.

According to the present invention the catalytic system at least includes one metallocene complex of general formula I or II.

$$(L(R)_a)_x MX_y \quad \text{I}$$

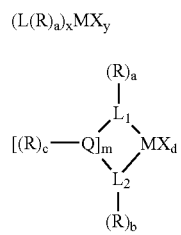

II wherein:

R, equal to or different from each other, is hydrogen or a radical which contains from 1 to 20 carbon atoms; this group optionally contains heteroatoms of groups 14 to 16 of the periodic table of the elements and boron; at least one group R contains a group $OSiR''_3$; preferably it is: hydrogen, $C_1-C_{20}$ alkyl, $C_3-C_{20}$ cycloalkyl, $C_6-C_{20}$ aryl, $C_7-C_{20}$ alkenyl, $C_7-C_{20}$ arylalkyl, $C_7-C_{20}$ arylalkenyl or alkylaryl, linear or branched or a group $SiR'_3$ wherein R' is $C_1-C_{20}$ alkyl, $C_3-C_{20}$ cycloalkyl, $C_6-C_{20}$ aryl, $C_7-C_{20}$ alkenyl, $C_7-C_{20}$ arylalkyl, $C_7-C_{20}$ arylalkenyl or alkylaryl, linear or branched or $OSiR''_3$, wherein R" is selected from the group comprising: $C_1$–$C_{20}$ alkyl, $C_3$–$C_{20}$ cycloalkyl, $C_6$–$C_{20}$ aryl, $C_7$–$C_{20}$ alkenyl, $C_7$–$C_{20}$ arylalkyl, $C_7$–$C_{20}$ arylalkenyl or alkylaryl, linear or branched.

Non limitative examples of R containing the group $OSiR''_3$ are:

—$CH_2$—$CH_2$—$OSiMe_3$; —$CH_2$—$CH_2$—$CH_2$—$OSiMe_3$; —$CH_2$—O—$CH_2$—$OSiMe_3$; —O—$CH_2$—$CH_2OSiMe_3$; —$SiMe_2$—$CH_2$—$CH_2$—$OSiMe_3$; —$CH_2$—$C_5H_5$—$CH_2$-$OSiMe_3$; —$CH(C_2H_5)$—$CH_2$—$OSi(C_5H_{11})_3$; —$C_5H_5$—$CH_2$—$OSi(C_5H_5)_3$; —$C_5H_5$—$C_5H_5$—$CH_2$—$OSi$($^iPr$)$_3$; —$C(CH_3)_2$—$CH_2$—$C_5H_5$—$CH_2$—$CH_2$—$OSi$($C_5H_{11}$)$_3$; —$C_5H_5$—$CH_2$—$CH_2$—$OSi(CH_2Ph)_3$; —$C(CH_3)_2$ —$C(CH_3)_2OSi(PhMe)_3$; —$CH(CH_3)$—$CH(CH_3)$—$OSi(C_2H_5)(Me)_2$.

Preferably the group R that contains $OSiR''_3$ is selected from the group comprising: —$CH_2$—$CH_2$—$OSiMe_3$, —$CH_2$—$CH_2$—$CH_2$—$OSiMe_3$, —$CH_2$—O—$CH_2$—$OSiMe_3$, —O—$CH_2$—$OSiMe_3$; —$SiMe_2$—$CH_2$—$CH_2$—$OSiMe_3$.

Q is selected from a group comprising: boron or an element from groups 14 or 16 of the periodic table; when m>1, the groups Q are equal to or different from each other; the free valences of every Q are filled with groups R according to the value of c index; two groups R are optionally united to form a ring from 5 to 8 atoms. m value can vary from 1 to 4 and it preferably is 1 or 2.

L, equal to or different from each other, is a cyclic organic group united to M through a π bond; it contains a cyclopentadienyl ring, that optionally is fused with one or more other rings to form for example: tetrahydroindenyl, indenyl, fluorenyl or octahidrofluorenyl group; or it is an atom from groups 15 or 16 of the periodic table; when it is an atom from groups 15 or 16 of the periodic table (heteroatom), it preferably is an oxygen or nitrogen atom, directly bonded to the metal.

$L_1$ and $L_2$, equal to or different from each other, have the same meaning of L; M is a metal from groups 3, 4, 10 of the periodic table, lanthanide or actinide; preferably it is Ti, Zr or Hf;

X, equal to or different from each other, is selected. from a group comprising: halogen, hydrogen, OR''', $N(R''')_2$, $C_1$–$C_{20}$ alkyl or $C_6$–$C_{20}$ aryl; wherein R''' is selected from the group comprising: $C_1$–$C_{20}$ alkyl, $C_3$–$C_{20}$ cycloalkyl, $C_6$–$C_{20}$ aryl, $C_7$–$C_{20}$ alkenyl, $C_7$–$C_{20}$ arylalkyl, $C_7$–$C_{20}$ arylalkenyl or alkylaryl, linear or branched;

x is 1 or 2, y is 2 or 3 in such a way that x+y=4 d ranges from 0 to 2;

a, b and c are integers from 0 to 10, in such a way that a+b+c≧1, the maximum value for a and b depends on the available positions in L, $L_1$ or $L_2$; for example, for the cyclopentadiene, in general formula I, 5 is the maximum value for a, on the contrary in the general formula II, for cyclopentadiene, 4 is the maximum value for a or b; for nitrogen in the general formula II, a or b is 1, for oxygen it is 0; the value of c index depends on the free valences of group Q, for example, if Q is equal to a silicon atom or carbon atom the value of c is 2; if Q is a boron atom the value of c is 1.

Examples of $[R)_cQ]_m$ when m is equal to 1 and c is equal to 2 are: $R_2Si$, $R_2C$.

Examples of $[(R)_cQ]_m$ when m is equal to 2 and c is equal to 2 are: $R_2Si$—$CR_2$, $R_2C$—$CR_2$, $R_2Si$—$SiR_2$.

Examples of $[(R)_cQ]_m$ when m is equal to 3 and c is equal to 2 or 1 are: $R_2Si$—O—$SiR_2$, $R_2Si$—O—$CR_2$, RB-O-BR.

The metallocene complexes belonging to the general formula I, where x=2, and those belonging to formula II where d=2 can be prepared through reaction of a metal compound of general formula $MX_n(E)_q$, wherein E is a linear or cyclic ether, q is a number between 0 and 4 and n is 3 or 4 with another compound of general formula $[(L(R)_a)]M'$ or $[(R)_aL_1$-$((R)_cQ)_m$-$L_2(R)_b]M'_2$ where M' is an alkali metal, preferably Li, Na or K. The preferred compound of the transition metal is tetrachloride and sometimes, when the metal is titanium, it is trichloride or its aduct with a cyclic ether such as tetrahydrofurane.

The reaction between the metal compound and the alkali metal derivative is preferably carried out in a dry nitrogen atmosplhere, by using anhydrous solvents such as linear or cyclic ethers such as dietylether, tetrahydrofurane or dioxane, or aromatic hydrocarbon such as toluene.

The alkali metal compound of formula $[(L(R)_a)]M'$ can be prepared from the compound of formula $L(R)_aH$ through reaction with a lithium alkyl, with a sodium or potassium hydride or directly with the metal.

On its turn, the ligand $L(R)_aH$, when L is or contains a cyclopentadienyl ring, can preferably be obtained from cyclopenadiene or indene through reaction of its sodium salts in the first case and potassium salt in the second case, with a compound R—S, where R has previously been defined and S is a proper leaving group such as halide or alkyl or aryl sulphonate. The reaction will be repeated as many time as necessary, according to the following scheme for a equal to 3

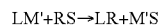

LM'+RS→LR+M'S

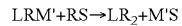

LRM'+RS→LR$_2$+M'S

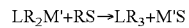

LR$_2$M'+RS→LR$_3$+M'S

The alkali metal compound $[(R)_aL_1$-$[(R)_cQ]_m$-$L_2(R)_b]M'_2$ can be obtained through reaction of two equivalents of a metallizing agent such as lithium alkyl, e.g. MeLi or BuLi, or alternatively sodium or potassium hydride, with a compound of formula $((R)_aHL_1$-$[(R)_cQ]_m$-$L_2H(R)_b)$. When a group L is an oxygen or nitrogen atom, the preferred metallizing agent is lithium alkyl. The compound of formula $[(R)_aHL_1$-$((R)_cQ)_m$-$L_2H(R)_b]$ can be obtained through reaction of the alkali metal compound $[L_1H(R)_a]M'$ or $[LH(R)_a]M'$ or mixtures thereof with a compound of formula S-$[(R)_cQ]_m$-S, where S is a proper leaving group, such as halogen (Cl, Br, I), or aryl or alkyl sulphonate.

The preferred metallocene complexes of formula I correspond to compounds wherein:

M is zirconium

R is $C_1$–$C_4$ alkyl, wherein at least one hydrogen of one R is substituted with $OSiR''_3$, wherein R'' is selected from the group comprising: methyl, etlhyl, propyl L is a cyclopentadienyl or indenyl group x=2 and y=2

The preferred complexes of general formula II, wherein $L_1$ and $L_2$ are cyclic organic compounds, correspond to compounds wherein:

M is zirconium $L_1$ and $L_2$ are cyclopentadienyl or indenyl groups

R is hydrogen, a $C_1$–$C_4$ alkyl wherein at least one hydrogen of one R is substituted with group $OSiR''_3$ or a group $SiR'_2$—$OSiR''_3$, wherein R'' is selected from the group comprising: metlhyl, ethyl, propyl $[(R)_cQ]_m$ is selected from the group comprising: $H_2C$—$CH_2$, CRH—$CH_2$, RHC–$SiR'_2$, $R_2C$—$SiR'_2$ or SiRR'.

The preferred complexes of general formula II wherein one of $L_1$ and $L_2$ is an oxygen or nitrogen atom correspond to compounds wherein:

The other group $L_1$ or $L_2$ is a cyclopentadienyl, indenyl or fluorenyl ring

M is titanium $[(R)_cQ]_m$ is $H_2C—CH_2$, $CRH—CH_2$, $RHC—SiR'_2$, $R_2C—SiR'_2$ or $SiRR'$.

The compounds of formula I or II can be supported on a proper inorganic support. As supports, any type of inorganic oxides can be used, for example inorganic oxides, such as: silica, alumina, silica alumina, aluminium phosphates and mixtures thereof, obtaining supported catalysts with contents in transition metals between 0.01 and 10% by weight, preferably between 1 and 4%.

A method that can be fit for preparing supported catalysts according to this invention consists in the impregnation, under anhydrous conditions and inert atmosphere, of the solution of any metallocene of formula I or II, or a mixture thereof, on the supporting material at a proper temperature, preferably between −20° C. and 90° C. The supported catalyst that contains the metallocene can be obtained through filtration and washing with a proper solvent, preferably an aliphatic or aromatic hydrocarbon without polar groups.

Another method that can properly be used consists in depositing the metallocene on the support by using a solution of the compound that has to be heterogenized, eliminating the solvent through evaporation and then warming the solid residue at a temperature between 25 and 150° C. Besides, the resulting residue, obtained by this process, can be subjected to washing and subsequent filtration.

The process can also be carried out in the presence of a cocatalyst that for example can be mixed with a metallocene in a proper solvent and then the resulting solution can be put in contact with the support.

The amount of the organometallic complex which can be anchored in these conditions directly depends on the concentration of the reactive groups present in the support. For this reason silica, for example, should preferably have been calcinated at a temperature between 600° C. and 800° C.

An advantageous aspect of this invention is that the fixation method, as a consequence of the reaction of groups R, which contain the —OSiR"$_3$ entity with reactive groups of the support surface, prevents the desorption of the supported metallocene complexes. This type of interaction represents the main difference between the organocomplexes heterogenization mechanism and other conventional methods, where the metallocene complex generally remains physisorbed on the support surface. The organocomplex fixation to the inorganic support is based on the reaction of the reactive groups of the support with the group —OSiR"$_3$ or groups of the metallocene, as it is described in FIG. IV.

Metallocene complexes of formula I or II, individually or supported, can be used in the presence of a cocatalyst for olefins polymerization or copolymerization, either in solution or suspension process.

When X is a halogen, OR'" or N(R'")$_2$ the preferred cocatalysts are alkylaluminoxane, especially methylaluminoxane compounds, when X is hydrogen or alkyl the preferred cocatalysts is a Lewis acid such as $B(C_6F_5)_3$. In addition mixtures of both aluminoxane and boron derivatives can be used as cocatalysts.

The most proper polymerization procedure can change according to the chosen type of polymerization process (solution, suspension or gas phase).

For the polymerization in solution, the cocatalyst can be mixed with a solution of a metallocene of formula I or II and a supplementary quantity of it can be added to the solution; or the catalyst can directly be added to the polymerization medium, which contains the cocatalyst.

For the polymerization in suspension, the cocatalyst can previously be mixed with the supported solid catalyst, can be added to the polymerization medium before the supported catalyst, or both operations can be sequentially carried out.

The process consists in putting in contact the monomer, or, in certain cases, the monomer and the comonomer, with a catalytic composition according to the present invention, that includes at least one metallocene complex of formula I or II, at a proper temperature and pressure.

The alpha-olefins that can be used as comonomers to obtain ethylene copolymers can be propylene, butene, hexene, octene or branched ones such as the 4-methyl-1-pentene and can be used in proportions from 0.1 to 70% by weight of the total of the monomers. In the case of homopolymerization of ethylene the density of polymers range between 0.950 and 0.965 g/cm$^3$ in the case of copolymerization of ethylene the density is as low as 0.900 g/cm$^3$.

To control the molecular weight of the obtained polymers, hydrogen can optionally be used as chain transfer agent in such proportions that the hydrogen partial pressure, with respect to the olefin one, is from 0.01 to 50%.

In the particular case of the polymerization technique known as suspension process or controlled particle morphology process, the used temperature will be between 30° C., and 100° C., the same which is typically used in gas phase, while for the solution process the usual temperature will be between 120° and 250° C.

The used pressure changes according to the polymerization technique; it ranges from atmospheric pressure to 350 MPa.

FIG. I shows examples of compounds according to formula I;

FIG. II shows examples of compounds according to formula II, wherein both $L_1$ and $L_2$ contain a cyclopentadienyl derivative.

In FIG. III there are examples of compounds according to formula II, wherein an group L is an oxygen or nitrogen atom and the other group contains a cyclopentadienyl derivative.

FIG. IV shows the reaction between the siloxane groups of the supports and the groups —OSiR"$_3$ of the organometallic complexes.

The following examples are described in order to better understand the invention. The materials, the chemical compounds and the conditions used in these examples are illustrative and do not limit the scope of the invention.

EXAMPLE 1 a) Preparation of (dimethyl)-(trimethylsiloxy)-silyl-cyclopentadiene

To a solution of 20.9 g (187 mmol) of sodium trimethylsilanolate in tetrahydrofurane, 30.3 g (191 mmol) of chlorocyclopentadienyl-dimethyl-silane in tetrahydrofurane is added at room temperature and a pink suspension immediately is formed. It is left reacting 12 hours. Then, it is neutralised with an ammonium chloride aqueous solution, the organic phase is extracted, dried with anhydrous magnesium sulphate and the solvent is eliminated under vacuum; an orange oil is recovered. This oil is distilled and the desired product is obtained as a pale yellow oil. ($T_b$: 60° C.; 0.014 bar (10 mmHg)). (31.6 g, 149 mmol. Yield: 80%). $^1$H-NMR (CDCl$_3$): 6.65 (m, 2H), 6.54 (m, 2H), 3.52 (s, 1H), 0.60 (s, 9H), −0.2 (s, 6H).

b) Preparation of potassium (dimethyl)-(trimethylsiloxy)-silyl-cyclopentadienide To a suspension of 0.6 g (15 mmol) of potassium hydride in tetrahydrofurane, a solution of 3.1 g of (dimethyl)-(trimethylsiloxy)-silyl-cyclopentadiene is added at −78° C. arid a strong $H_2$ evolution is observed. It is maintained under stirring until room temperature is achieved. It is left reacting for about 1 hour until all the potassium hydride is reacted. The tetrahydrofurane solution is concentrated under vacuum and a clear yellow solid is obtained. (3.45 g, 13.8 mmol. Yield: 92%).

c) Preparation of cyclopentadienyl [((dimethyltrimethylsiloxy)-silyl)-cyclopentadienyl] zirconium dichloride To 5.2 g (14 mmol) of an adduct of cyclopentadienyl zirconium trichloride with dimethoxyethane in toluene, a suspension of 3.45 g (13.8 mmol) of potassium dimethyltrimethylsiloxy-silyl-cyclopentadienide in toluene is added at −78° C. The suspension is maintained under stirring for 24 hours; after settling, a yellow solution is filtered. The yellow solution is concentrated up to 20 ml; then, some hexane is added and a crystalline white solid precipitates. (3.1 g, 7.1 mmol. Yield: 51%). $^1$H-NMR ($C_6D_6$): 6.45 (t, 2H), 6.03 (s, 5H), 5.95 (t, 2H), 0.39 (s, 6H), 0.09 (s, 9H). $^{13}$C-NMR ($C_6D_6$): 125.4, 123.6, 117.3, 115.9, 2.0. Mass spectrum. $M^+$-15: m/e 422.9 (32%).

EXAMPLE 2 a) preparation of bis[((dimethyltrimethylsiloxy)-silyl)-cyclopentadienyl] zirconium dichloride To 0.93 g (4 mmol) of zirconium tetrachloride a suspension of 2.02 g (8 mmol) of potassium dimethyltrimethylsiloxy-silyl-cyclopentadienide in hexane is added at −78° C. The formation of a yellow suspension is observed. It is left under stirring for 12 hours. Then the solution is filtered and concentrated and a yellowish crystalline solid is obtained. (0.75 g, 1.3 mmol. Yield: 32%). $^1$H-NMR ($C_6D_6$): 6.58 (t, 2H), 6.13 (t, 2H), 0.45 (s, 6H), 0.14 (s, 9H). $^{13}$C-NMR ($C_6D_6$): 126.2, 124.1, 116.5, 2.13, 2.06. Mass spectrum. $M^+$-15: m/e 569 (15%)

EXAMPLE 3 a) Preparation of 2-bromo-1-trimethylsiloxyethane

To 125 g (888 mmol) of 2-bromo-ethanol, 95 ml (1450 mmol) of hexamethyldisilazane are slowly added at 0° C. Ammonia evolution is immediately observed. The reaction is maintained under stirring for 12 hours and a colourless oil is obtained. (168.8 g 856 mmol. Yield:96%) $^1$H-NMR ($CDCl_3$): 3.66 (t, 2H), 3.40 (t, 2H), 0.14 (s, 9H).

b) Preparation of (2-trimethylsiloxy-ethyl)-cyclopentadiene 150 ml of a 2.3 M sodium cyclopentadienide solution in tetrahydrofurane (346 mmol) is slowly added to a solution of 68.2 g (346 mmol) 2-trimethylsiloxy-1-bromo-ethane in tetrahydrofurane. The immediate formation of a pinkish solid is observed. The reaction is maintained under stirring for 12 hours. Then, an ammonium chloride aqueous solution is added. The organic phase is extracted, dried with magnesium sulphate and the volatile part is distilled under vacuum, obtaining an orange oil. This oil is distilled in order to obtain a colourless oil. ($T_b$.: 63–65° C., 0.02 bar (15 mmHg.)). (40.3 g, 221 mmol. Yield:64%). $^1$H-NMR ($CDCl_3$): 6.50–6.00 (m,3H), 3.75 (m, 2H), 2.95 (m, 2H), 2.65 (m, 2H), 0.15 (s, 9H).

c) Preparation of lithium (2-trimethylsiloxy-ethyl)-cyclopentadienide

To 7.33 g of (2-trimethylsiloxy-ethyl)-cyclopentadiene in ether, 16 ml of a 2.5 M butyllithium solution in hexane (40 mmol) is added. The addition is realised at −78° C. The immediate formation of a white solid and butane evolution are observed. It is maintained reacting for 3 hours. Then it is dried; the resulting solid washed with hexane, leaving a powdery white solid. (6.19 g, 33 mmol, Yield: 82%).

d) Preparation of bis[(2-trimethylsiloxy-ethyl)-cyclopentadienyl] zirconium dichloride To 1.37 g (5.9 mmol) of zirconium tetrachloride, a suspension of 2.2 g (11.7 mmol) of lithium (2-trimethylsiloxy-ethyl)-cyclopentadienylide is added at −78° C. An orange suspension is immediately formed. The reaction is maintained under stirring for 12 hours. Finally, the solution is filtered, concentrated to dryness, and a yellow oily solid is recovered, which is mixed with hexane and a yellow solid is obtained. (1.05 g, 2 mmol. Yield: 34%). $^1$H-NMR ($C_6D_6$): 6.02 (t, 2H), 5.72 (t, 2H), 3.62 (t, 2H), 2.89 (t, 2H), 0.05 (s, 9H). $^{13}$C-NMR ($C_6D_6$): 117.7, 112.0, 111.2, 62.6, 34.0, −0.45. Mass spectrum. $M^+$-15: (509). 1.24%.

EXAMPLE 4 a) Preparation of potassium (2-trimethylsiloxy-ethyl)-cyclopentadienide

To a suspension of 0.5 g (12.4 mmol) of potassium hydride in tetrahydrofurane, 2.25 g (12.4 mmol) of (2-trimethylsiloxy-ethyl)-cyclopentadiene in tetrahydrofurane is added. The reaction is maintained under stirring for 2 hours and then the volatile compounds are eliminated, leaving an oily solid which is washed with hexane in order to obtain a brown solid. (2.2 g Yield: 81%)

b) Preparation of cyclopentadienyl ((2-trimethylsiloxy-ethyl)-cyclopentadienyl) zirconium dichloride To a suspension of 3.52 g (10 mmol) of an adduct of cyclopentadienyl zirconium trichloride with dimethoxyethane in toluene, a suspension of 2.2 g (10 mmol) of potassium (2-trimethylsiloxy-ethyl)-cyclopentadienide in toluene is added. The addition is carried out at −78° C. An orange-brown suspension is immediately formed; it is maintained under stirring for 12 hours; then it is left settling and it is filtered. The obtained orange solution is concentrated up to 5 ml and hexane is added, so that a brown solid is obtained. (1.1 g, 2.7 mmol. Yield: 27%). $^1$H-NMR: 6.00 (t, 2H), 5.87 (s, 5H), 5.67 (t, 2H), 3.66 (t, 2H), 2.92 (t, 2H), 0.11 (s, 9H). Mass spectrum. $M^+$-65: (343): 33%.

EXAMPLE 5 a) Preparation of 3-bromo-1-trimethylsiloxypropane

To 12.2 g (76 mmol) of hexamethyldisilazane, 21 g (151 mmol) of 3-bromo-1-propanol is added. Ammonia evolution is immediately observed. The reaction is maintained under stirring for 2 hours and 24.5 g (148 mmol) of the desired compound is finally obtained. Yield: 98%. $^1$H-NMR (CDCl$_3$): 3.74 (t, 2H), 3.55 (t, 2H), 2.09 (m, 2H), 0.14 (s, 9H).

b) Preparation of (3-trimethylsiloxypropyl)-cyclopentadiene

To 50 ml of a 2.3 M solution of sodium cyclopentadienylide (115 mmol), a solution of 24.3 g (115 mmol) of 3-bromo-1-trimethylsiloxypropane in tetrahydrofurane is added. The quick formation of a pinkish solid is observed. The reaction is maintained under stirring for 12 hours and then it is neutralised with an ammonium chloride solution; the organic phase is extracted and concentrated to dryness in order to give an orange oil. (9.8 g, 50 mmol. Yield: 43%). $^1$H-NMR (CDCl$_3$): 6.47–6.00 (m, 3H), 3.62 (m, 2H), 2.95 (m, 1H), 2.87 (m, 1H), 2.43 (m, 2H), 1.80 (m, 2H), 0.17 (s, 9H).

c) Preparation of lithium (3-trimethylsiloxy-propyl)-cyclopentadienide

To a solution of 2.62 g (13.4 mmol) of (3-trimethylsiloxypropyl)-cyclopentadiene in ether, 5.36 ml of a 2.5 M (13.4 mmol) butyl lithium solution in hexane is added at −78° C. The immediate formation of a white solid is observed. The reaction is maintained under stirring for 2 hours; then, the white suspension is brought to dryness, the resulting solid is washed twice with hexane and a powdery white solid is obtained. (2.3 g, 11.4 mmol. Yield: 85%).

d) Preparation of bis[(3-trimethylsiloxypropyl)-cyclopentadienyl] zirconium dichloride To a suspension of 1.33 g (5.7 mmol) of zirconium tetrachloride, a suspension of 2.3 g (11.4 mmol) of lithium (3-trimethylsiloxypropyl)-cyclopentadienylide is added at −78° C. An orange suspension is immediately formed and the reaction is maintained under stirring for 12 hours. It is subsequently filtered and the resulting solution is concentrated up to 5 ml, hexane is added and a microcrystalline white solid is formed. (1.27 g, 2.3 mmol Yield:40%). $^1$H-NMR (C$_6$D$_6$): 5.95(t, 2H), 5.77 (t, 2H), 3.52 (m, 2H), 2.81 (m, 2H), 1.80 (m, 2H), 0.15 (s, 9H). Mass spectrum: M$^+$-15: (357): 59%.

EXAMPLE 6 a) Preparation of potassium (3-trimethylsiloxypropyl)-cyclopentadienide

To a suspension of 0.4 g (10 mmol) of potassium hydride in tetrahydrofurane, 1.96 g (10 mmol) of a (3-trimethylsiloxy-propyl)-cyclopentadiene in tetrahydrofurane is added. The reaction is maintained under stirring for 2 hours. Subsequently, the resulting suspension is concentrated to dryness, leaving an oily solid that, when it is washed with hexane, gives a cream-coloured solid. (1.6 g, 7 mmol. Yield:70%).

b) Preparation of [cyclopentadienyl (3-trimethylsiloxypropyl)-cyclopentadienyl]zirconium dichloride To a suspension of 2.46 g (7 mmol) of cyclopentadienyl zirconium trichloride in toluene, a suspension of 1.6 g (7 mmol) of potassium (3-trimethylsiloxypropyl)-cyclopentadienide in toluene is added. A yellow-brown-coloured suspension immediately precipitates. The reaction is maintained for 12 hours. Subsequently, the solution is filtered and concentrated and a crystalline white solid is formed (0.8 g, 2 mmol, 28%). $^1$H-NMR (C$_6$D$_6$): 5.87 (t, 2H), 5.65 (t, 2H), 3.46 (m, 2H), 2.74 (m, 2H), 1.73 (m, 2H), 0.14 (s, 9H). $^{13}$C-NMR (C$_6$D$_6$): 11.6.9, 115.0, 114.7, 112.2, 61.8, 33.6, 26.8, −0.393. Mass spectrum: M$^+$-65(356): 30%.

EXAMPLE 7

Heteroytenization of bis[(3-trimethylsiloxypropyl)-cyclopentadienyl] zirconium dichloride on silica To a suspension of 12 g of silica (Grace XPO-2407, calcined at 800° C.) in 70 ml of toluene, a solution of 4.1 g of the compound prepared according to the description in example 5d in 20 ml of toluene is added. The reaction mixture is maintained under stirring at 25° C. for 18 hours. The solution is separated from the solid through filtration.

Then, the solid is washed with various fractions of toluene, up to a total volume of 500 ml and dried under vacuum for 18 hours. The Zr content in the sample was determined through ICP and resulted to be 1.7%.

When the same sample was washed with 50 ml (in three fractions) of a MAO 1.5 M solution in toluene, the Zr percentage which was left in the sample lowered to 1.1%.

EXAMPLE 8

Heterogenization of [cyclopentadienyl (3-trimethylsiloxypropyl)-cyclopentadienyl] zirconium dichloride on silica To a suspension of 3 g of silica, in about 70 ml of dry toluene, 0.5 g (1.32 mmol) of a compound prepared according to example 6b is added.

The reaction mixture was maintained under stirring at 25° C. for about 18 hours. The solid was separated from the solution through filtration. Then, the resulting solid was washed with a total volume of 500 ml of toluene and dried under vacuum for 12 hours. The zirconium analysis through ICP gave 1.7% in the sample.

EXAMPLE 9

Heterogenization of bis[(2-trimethylsiloxyethyl)-cyclopentadienyl] zirconium dichloride To a suspension of 3 g of silica (Grace XPO-2407 calcinated at 800° C.) in 70 ml of toluene, a solution of 0.5 g of the compound described in example 3d in 20 ml of toluene is added. The reaction mixture was maintained at 40° C. for 18 hours under stirring. The solution was separated from the solid through filtration. The solid resulting from the reaction was analysed through ICP, which showed that the zirconium percentage in the sample was 2.75%.

Then, the solid was washed with three different fractions of toluene, up to a total volume of 500 ml and dried under vacuum for 18 hours. The Zr content in the sample was determined through ICP and gave 2.79% of zirconium.

EXAMPLE 10

Heterogenisation of bis[(3-trimethylsiloxypropvl)-cyclopeiitadienyl] zirconium dichloride on aluminum phosphate The compound was heterogenized through the same process used to support it on silica, according to the description in example 7, but using aluminium phosphate (Grace APGE) instead of silica (Grace XPO-2407).

The Zr content in the sample was determined through X rays fluorescence and gave 2% of zirconium.

EXAMPLE 11

Ethylene Polymerization

The ethylene polymerization reactions were completed in a 1 litre-capacity Buchi reactor in anhydrous conditions. The reactor, charged with 600 ml of dry and degassed heptane, was conditioned at 70° C. Before pressurising the reactor with ethylene the cocatalyst was injected at a pressure of 1 atm. Then, the reactor was pressurised up to 3.75 atm. At the end, the catalyst was injected by using 0.25 atm of ethylene extra pressure. The polymerization reactions is maintained at these pressure (4 atm) and temperature (70° C.) conditions. The suspension was stirred with the help of a stirring bar at 1200 rpm for 15 or 30 minutes.

13 ml (31.8 mmol Al) of MAO from a 10% solution of aluminium in toluene (commercialized by Witco) were injected in the reactor; 0.1 g of [cyclopentadienyl (3-trimethylsiloxypropyl) cyclopentadienyl] zirconium dichloride catalyst supported on silica, prepared according to the description in example 8 (18.24 μmol Zr), is added to this solution. Once completed, the polymerization reaction was maintained under stirring at a temperature of 70° C. and 4 atm of ethylene pressure for 30 minutes. At the end of the reaction the pressure was rapidly reduced and the reaction was stopped by adding acidified methanol. 5.21 g of polymer having $M_w$=157.824 is obtained (Activity: $1.4\times10^5$ g PE/(mol Zr*hr*atm).

EXAMPLE 12

Ethylene copolymerization with 1-hexene

The copolymerization reaction is carried out in the same conditions as those described for ethylene polymerization, after the comonomer initial addition in the reactor.

10 ml of 1-hexene (24.2% by mol of comonomer in the feeding) and 13 ml of MAO, from an aluminium 10% solution (31.8 mmol Al), is injected in the reactor. 0.1 g of a [cyclopentadienyl (3-trimethylsiloxypro cyclopentadienyl] zirconium dichloride catalyst prepared according to the description in example 8 (18.4 μmol Zr) supported on silica is added to this solution. The polymerization reaction was maintained at a temperature of 70° C. and 4,132 bar (4 atm) of ethylene pressure for 30 minutes. At the end, the pressure was rapidly reduced and the reaction was stopped by adding acidified methanol. 5.14 grams of copolymer with: Mn=41970, Mw=220877, Mw/Mn=5.26 and 0.92% molar of hexene is obtained. (Activity: $1.41\times10^5$ g PE/(mol Zr*hr*atm).

EXAMPLE 13

Ethylene copolymerization with 1-hexene

Ethylene and 1-hexene were copolymerized. To do this, the same method as the previous example (number 12) is used, but with the proviso that once the solvent is added and before pressurising the reactor, 4 ml of dry and recently distilled 1-hexene (12% of hexene in the feeding) is added. 13 ml of a MAO solution in toluene (1.5 M of total aluminium) and 0.1 g of catalyst catalyst prepared according to the description in example 8 are used. After 30 minutes of polymerization 1.47 g of polymer is obtained ($1.65\times10^5$ g PE/mol Zr*h*atm). The 1-hexene content in the copolymer, determined by $^{13}$C-RMN, was 0.49% molar, distributed at random.

EXAMPLE 14

Ethylene copolymerization With 1-hexene

Ethylene and 1-hexene were copolymerized. To do this, the same method as example n. 12 was used, but with the proviso that once the solvent is added and before pressurising the reactor, 16 ml of dry and recently distilled 1-hexene (33.7% of hexene in the feeding) is added. 13 ml of a MAO solution in toluene (1.5 M of total aluminium) and 0.1 g of the catalyst are used. After 30 minutes of polymerization 1.80 g of polymer were obtained ($2.02\times10^5$ g PE/mol Zr*h*atm). The 1-hexene content in the copolymer, determined by $^{13}$C-NMR, was 1.33% molar, distributed at random.

EXAMPLE 15

Ethylene Polymerization

In the reactor 13 ml (31.8 mmol Al) of MAO, from a 10% solution of aluminium in toluene (commercialised by Witco), are injected. 0.1 g of a [cyclopentadienyl (3-trimethylsiloxypropyl) cyclopentadienyl] zirconium dichloride catalyst prepared according to the description in example 10 (35.77 μmol Zr) supported on aluminium phosphate is added to this solution. The polymerization reaction was kept at a temperature of 70° C. and 4,132 bar (4 atm) of ethylene pressure for 30 minutes. When the reaction was considered completed, the pressure was rapidly reduced and acidified methanol was added. 2.16 grams of polyethylene was obtained. Activity: $0.24\times10^4$ g PE/(mol Zr*hr*atm).

EXAMPLE 16

Heterogenization of bis[(3-trimethylsiloxypropyl) cyclopentadienyl] zirconium dichloride on silica 0.220 g of bis[(3-trimethylsiloxypropyl) cyclopentadienyl] zirconium dichloride is dissolved in 15 ml of toluene, then, 0.7 ml of a 10% MAO solution in toluene (commercialized by Witco) is added and the mixture is maintained under stirring at room temperature. 15 minutes later, the resulting solution is poured in a 100 ml flask, that contains 3 g of silica XPO-2407 (commercialized by Grace), which has previously been calcinated at a temperature of 200° C. and it is maintained under mechanic stirring for 1 hour at a temperature of 40° C. Once the reaction time has gone by, the solid is separated through filtration and washed with consecutive fractions of toluene up to a total volume of 1l.

The heterogeneous catalyst is finally dried under vacuum for 24 hours. The Zr and Al content determined through ICP is 1.15% and 0.7% respectively.

EXAMPLE 17

Heterogenization of bis[(3-trimethylsiloxypropyl) cyclopentadienyl] zirconium dichloride on silica The process for the heterogenization of bis[(3-trimethylsiloxypropyl) cyclopentadienyl] zirconium dichloride is the one described in example 16, but the silica is previously treated under vacuum before being put in contact with the premixture of the organo-metallic compound and the MAO. The Zr and Al content determined through ICP is 1.2% and 0.7% respectively.

EXAMPLE 18

The polymerization reaction is carried out according to the method and the conditions described in example 11, but the reactor temperature is 90° C. 10 ml of a 10% MAO solution in toluene (commercialized by Witco) (15 mmol of Al) and 0.079 g (0.01 mmol of Zr) of the heterogeneous catalyst prepared according to example 16 are injected in the reactor. The polymerization reaction is maintained at a temperature of 90° C. and at an ethylene pressure of 4 atm for 15 minutes. At the end of the reaction the reactor pressure is reduced and acidified methanol is added. 2.4 grams of polymer with Mw=165.600 is obtained.

EXAMPLE 19

The polymerization reaction is carried out according to the method and the conditions described in example 18. 10 ml of a 10% MAO solution in toluene (commercialized by Witco) (15 mmol of Al) and 0.075 g (0.01 mmol of Zr) of the heterogeneous catalyst prepared according to example 17 are injected in the reactor. The polymerization reaction is maintained at a temperature of 90° C. and at an ethylene pressure 4 atm for 15 minutes. At the end of the reaction the reactor pressure is reduced and acidified methanol is added. 2.8 g of polymer is obtained.

What is claimed is:

1. Catalyst component for the polymerization of alpha-olefins in solution, in suspension, in gas phase at low and high pressure and temperature or in mass at high pressures and high or low temperatures, wherein the catalyst component is defined by general formulas I or II $(L(R)_a)_x MX_y$  I

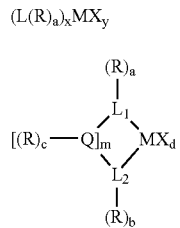

II wherein:
R equal to or different from each other, is hydrogen or a radical which contains from 1 to 20 carbon atoms; this group contains heteroatoms of groups 14 to 16 of the periodic table of the elements and boron;

at least one group R contains a group OSiR"$_3$, wherein R" is $C_1$–$C_{20}$ alkyl, $C_3$–$C_{20}$ cycloalkyl, $C_6$–$C_{20}$ aryl, $C_7$–$C_{20}$ aklenyl, $C_7$–$C_{20}$ aryalkyl, or $C_7$–$C_{20}$ arylalkenyl, linear or branched; Q is selected from a group consisting of: boron and an element from groups 14 or 16 of the periodic table;

m ranging from 1 to 4;

groups Q are equal to or different from each other; the free valences of every Q are filled with groups R according to the value of c index;

two groups R are united to form a ring from 5 to 8 atoms;

L, equal to or different from each other, is a cyclic organic group united to M through a π bond, it contains a cyclopentadienyl ring, that is fused with one or more other rings, or it is an atom from groups 15 or 16 of the periodic table;

$L_1$ and $L_2$, equal to or different from each other, have the same meaning as L;

M is a metal from groups 3, 4, or 10 of the periodic table, lanthanide or actinide;

X, equal to or different from each other, is halogen, hydrogen, OR''', N(R''')$_2$, $C_1$–$C_{20}$ alkyl or $C_6$–$C_{20}$ aryl, wherein R''' is $C_1$–$C_{20}$ alkyl, $C_3$–$C_{20}$ cycloalkyl, $C_6$–$C_{20}$ aryl, $C_7$–$C_{20}$ alkenyl, $C_7$–$C_{20}$ arylalkyl, $C_7$–$C_{20}$ arylalkenyl or alkylaryl, linear or branched;

x is 1 or 2, y is 2 or 3 such that x+y=4;

d ranges from 0 to 2;

a, b and c are integers from 0 to 10, such that a+b+c≧1.

2. Catalyst component according to claim 1 wherein R is hydrogen, $C_1$–$C_{20}$ alkyl, $C_3$–$C_{20}$ cycloalkyl, $C_6$–$C_{20}$ aryl, $C_7$–$C_{20}$ alkenyl, $C_7$–$C_{20}$ arylalkyl, $C_7$–$C_{20}$ arylalkenyl or alkylaryl, linear or branched or a group SiR'$_3$ wherein R' is $C_1$–$C_{20}$ alkyl, $C_3$–$C_{20}$ cycloalkyl, $C_6$–$C_{20}$ aryl, $C_7$–$C_{20}$ alkenyl, $C_7$–$C_{20}$ arylalkyl, $C_7$–$C_{20}$ arylalkenyl or alkylaryl, linear or branched or OSiR"3; at least one group R contains a group OSiR"$_3$, wherein R" is $C_1$–$C_{20}$ alkyl, $C_3$–$C_{20}$ cycloalkyl, $C_6$–$C_{20}$ aryl, $C_7$–$C_{20}$ alkenyl, $C_7$–$C_{20}$ arylalkyl, $C_7$–$C_{20}$ arylalkenyl or alkylaryl, linear or branched; all these groups contain heteroatoms of groups 14 to 16 of the periodic table of the elements and boron.

3. Catalyst component according to claim 1 wherein M is selected from the group consisting of: Ti, Zr and Hf.

4. Catalyst component according to claim 1 wherein the group R containing the group OSiR" is selected from the group consisting of: CH$_2$—CH$_2$—OSiMe$_3$, —CH$_2$—CH$_2$—CH$_2$OSiMe$_3$, —CH$_2$—O—CH$_2$—OSiMe$_3$, —O—CH$_2$—CH$_2$—OSiMe$_3$, and —SiMe$_2$—CH$_2$—CH$_2$—OSiMe$_3$.

5. Catalyst component according to claim 1 characterized in that in the general formula I, L is cyclopentadienyl or indenyl; M is zirconium; x is 2; y is 2; R is C1–C4 alkyl, wherein at least one hydrogen of one R is substituted with OSiR"3 wherein R" is selected from the group consisting of: Me, Et, and Pr.

6. Catalyst component according to claim 1 wherein in the general formula II, M is zirconium; L1 and L2 are cyclopentadienyl or indenyl group; R is hydrogen, a $C_1$–$C_4$ alkyl wherein at least one hydrogen of one R is substituted with OSiR"$_3$ or a SiR'$_2$—OSiR"$_3$ group, wherein R" is selected from the group comprising: methyl, ethyl, propyl; [(R)$_c$Q]$_m$ is H$_2$C—CH$_2$, CRH—CH$_2$, RHC—SiR'$_2$, R$_2$C—SiR'$_2$ or SIRR'.

7. Catalyst component according to claim 1 wherein in the general formula II, M is titanium; L$_2$ is an oxygen or a nitrogen atom; L$_1$ is a cyclopentadienyl, indenyl or fluorenyl ring; [(R)cQ]m is H$_2$C—CH$_2$, CRH—CH$_2$, RHC—SiR'$_2$, R$_2$C—SiR'$_2$ or SiRR'.

8. Catalyst component according to claim 1, wherein the catalyst component of formula I or II is supported on a porous inorganic solid.

9. Catalyst component according to claim 8 wherein the porous inorganic solid is selected from the group consisting of: silica, aluminia, silica-aluminia, aluminium phosphates and mixtures thereof.

10. Process for the preparation of a solid catalyst component comprising the following steps:
   a) impregnation, under anhydrous conditions and inert atmosphere, of a solution of at least one catalyst component wherein the solid catalyst component is defined by the general formula I or II

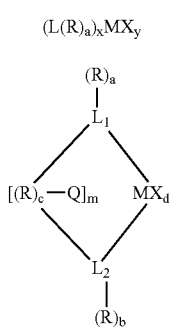

wherein:
   R equal to or different from each other, is hydrogen or a radical which contains from 1 to 20 carbon atoms; this group contains heteroatoms of groups 14 to 16 of the periodic table of the elements and boron;
   at least one group R contains a group $OSiR''_3$, wherein R'' is $C_1-C_{20}$ alkyl, $C_3-C_{20}$ cycloalkyl, $C_6-C_{20}$ aryl, $C_7-C_{20}$ aklenyl, $C_7-C_{20}$ arylalkyl, or $C_7-C_{20}$ arylalkenyl, linear or branched: Q is selected from a group consisting of: boron and an element from groups 14 or 16 of the periodic table;
   m ranging from 1 to 4:
   groups Q are equal to or different from each other; the free valences of every Q are filled with groups R according to the value of c index;
   two groups R are united to form a ring from 5 to 8 atoms;
   L, equal to or different from each other, is a cyclic organic group united to M through a π bond, it contains a cyclopentadienyl ring, that is fused with one or more other rings, or it is an atom from groups 15 or 16 of the periodic table;
   $L_1$ and $L_2$, equal to or different from each other, is the same as L;
   M is a metal from groups 3, 4, or 10 of the periodic table, lanthanide or actinide;
   X, equal to or different from each other, is halogen, hydrogen, OR''', $N(R''')_2$, $C_1-C_{20}$ alkyl or $C_6-C_{20}$ aryl, wherein R''' is $C_1-C_{20}$ alkyl, $C_3-C_{20}$ cycloalkyl, $C_6-C_{20}$ aryl, $C_7-C_{20}$ alkenyl, $C_7-C_{20}$ arylalkyl, $C_7-C_{20}$ arylalkenyl or alkylaryl, linear or branched;
   x is 1 or 2, y is 2 or 3 such that x+y=4;
   d ranging from 0 to 2;
   a, b an c being integers from 0 to 10, such that a+b+c>1.
   a) filtration and
   b) washing with a solvent, selected from aliphatic or aromatic hydrocarbon.

11. Process for the preparation of a solid catalyst component comprising the following steps:
   a) depositing a catalyst component 1 wherein the solid catalyst component is defined by general formula I or II

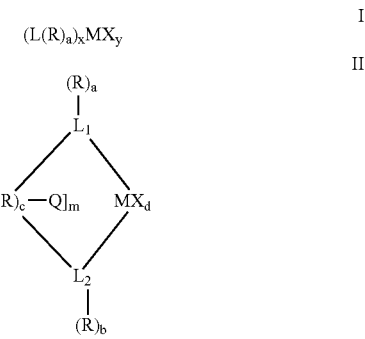

wherein:
   R equal to or different from each other, is hydrogen or a radical which contains from 1 to 20 carbon atoms; this group contains heteroatoms of groups 14 to 16 of the periodic table of the elements and boron;
   at least one group R contains a group $OSiR''_3$, wherein R'' is $C_1-C_{20}$ alkyl, $C_3-C_{20}$ cycloalkyl, $C_6-C_{20}$ aryl, $C_7-C_{20}$ aklenyl, $C_7-C_{20}$ arylalkyl, or $C_7-C_{20}$ arylalkenyl, linear or branched: Q is selected from a group consisting of: boron and an element from groups 14 or 16 of the periodic table;
   m ranging from 1 to 4;
   groups Q are equal to or different from each other; the free valences of every Q are filled with groups R according to the value of c index;
   two groups R are united to form a ring from 5 to 8 atoms;
   L, equal to or different from each other, is a cyclic organic group united to M through a π bond, it contains a cyclopentadienyl ring, that is fused with one or more other rings, or it is an atom from groups 15 or 16 of the periodic table;
   $L_1$ and $L_2$, equal to or different from each other, is the same as L;
   M is a metal from groups 3, 4, or 10 of the periodic table, lanthanide or actinide;
   X, equal to or different from each other, is halogen, hydrogen, OR''', $N(R''')_2$, $C_1-C_{20}$ alkyl or $C_6-C_{20}$ aryl, wherein R''' is $C_1-C_{20}$ alkyl, $C_3-C_{20}$ cycloalkyl, $C_6-C_{20}$ aryl,
   $C_7-C_{20}$ alkenyl, $C_7-C_{20}$ arylalkyl, $C_7-C_{20}$ arylalkenyl or alkylaryl, linear or branched;
   x is 1 or 2, y is 2 or 3 such that x+y=4;
   d ranging from 0 to 2;
   a, b an c being integers from 0 to 10, such that a+b+c>1 on the support, by using a solution of the compound to heterogenize;
   a) eliminating the solvent through evaporation; and
   b) warming the solid residue up to temperature between 25° C. and 150° C.

12. Process for the preparation of a solid catalyst component according to claim 10 wherein before step a) the catalyst component is mixed with a cocatalyst.

13. Polymerization catalyst comprising the catalyst component according to claim 1 and a cocatalyst.

14. Polymerization catalyst according to claim 13, wherein the cocatalyst is selected from a group consisting of: alkylaluminoxane, boron compound, and a mixture thereof.

15. Process for the polymerization of alpha-olefins in solution, in suspension, in gas phase at low and high pressure and temperature or in mass at high pressures and high or low temperatures, further comprising monomers, wherein the monomers are put in contact in the presence of a catalyst of claim 13.

16. Process for the polymerization of alpha-olefins in solution, in suspension, in gas phase at low and high pressure and temperature or in mass at high pressures and high or low temperatures according to claim 15 wherein the monomer is ethylene.

17. Process for the polymerization of alpha-olefins in solution, in suspension, in gas phase at low and high pressure and temperature or in mass at high pressures and high or low temperatures according to claim 15 further comprising a comonomer, wherein the monomer is ethylene and the comonomer is selected from the group consisting of: propylene, butene, hexene, octene and 4-methyl-1-pentene.

18. Process for the polymerization of alpha-olefins in solution, in suspension, in gas phase at low and high temperature or in mass at high pressures and high or low temperatures according to claim 17 wherein the comonomer is used in proportions from 0.1 to 70% by weight of the total of the monomers.

* * * * *